United States Patent [19]

Messing et al.

[11] 3,983,000

[45] Sept. 28, 1976

[54] BONDING PROTEINS TO INORGANIC SUPPORTS

[75] Inventors: Ralph A. Messing; Gerald Odstrchel, both of Horseheads, N.Y.

[73] Assignee: Corning Glass Works, Corning, N.Y.

[22] Filed: Apr. 1, 1976

[21] Appl. No.: 672,633

[52] U.S. Cl. .................................. 195/63; 195/68; 260/112 R; 195/DIG. 11
[51] Int. Cl.² .......................................... C07G 7/02
[58] Field of Search ................ 195/63, 68, DIG. 11; 260/112 R

[56] References Cited

UNITED STATES PATENTS 3,930,951  1/1976  Messing .............................. 195/63

*Primary Examiner*—Lionel M. Shapiro
*Attorney, Agent, or Firm*—James A. Giblin; Clinton S. Janes, Jr.; Clarence R. Patty, Jr.

[57] ABSTRACT

Proteins such as enzymes or antibodies can be immobilized in a biologically active state on various inorganic supports via an intermediate residue of o-dianisidine.

12 Claims, No Drawings

BONDING PROTEINS TO INORGANIC SUPPORTS

BACKGROUND OF THE INVENTION

1. Field

This invention is concerned generally with the field of immobilized proteins and specifically with enzymes and immune bodies which have been immobilized on inorganic support materials.

2. Prior Art

The desirability of immobilizing enzymes, antibodies, and other proteins for repetitive use and/or ease of handling is well known. Proteins have been immobilized or fixed on a wide variety of materials, both organic (e.g. U.S. Pat. No. 3,705,084 to Reynolds) and inorganic (e.g. U.S. Pat. No. 3,519,538 to Messing et al. disclosing enzymes bound via silanes and U.S. Pat. No. 3,652,761, to Weetall disclosing antibodies bound via silanes). See also, U.S. Pat. No. 3,850,751, to Messing disclosing enzymes bonded via adsorption to certain inorganics and U.S. Pat. No. 3,930,951 to Messing disclosing the use of another intermediate, 4,4'-bi (methoxybenzenediazonium chloride) or BMBD, to bond enzymes to various inorganics.

Although bonding by adsorption or via covalent bonds both have advantages and disadvantages relative to each other, it can be appreciated that, in general, bonding via chemical coupling means provides a stronger bond which is not subject to such factors as pH change. Hence, considerable attention has been directed toward finding relatively inexpensive "coupling agents" which can be used as intermediate links between proteins and various inorganic supports. Although substances known as silane coupling agents have been used as coupling agents for some time now, such materials are relatively expensive and must often be chemically modified after attachment to the inorgainic, but before reaction with the protein, thus adding an undesirable processing step and added cost. The BMBD compound disclosed recently in U.S. Pat. No. 3,930,951 offers some advantages over silane coupling agents but it is still rather expensive.

We have now found there exists an intermediate coupling agent which is relatively inexpensive and requires little or no modification prior to protein bonding. Details of our method of using such coupling agent to bond a variety of proteins are disclosed herein.

SUMMARY OF INVENTION

Our method of bonding proteins to inorganic support materials to form composities of immobilized biologically active proteins comprises the steps of reacting a high surface area, essentially water insoluble inorganic support material having available oxide or hydroxide surface groups with a solution of o-dianisidine under conditions sufficient to form a support coated with residues of o-dianisidine, and then reacting the coated support with an aqueous solution of the proteins to be bonded. In preferred embodiments, the inorganic support has a high surface area (>0.2 m²/g) and is siliceous.

SPECIFIC EMBODIMENTS

The carriers which can be reacted with the o-dianisidine solution include any essentially water-insoluble inorganics having available surface oxide or hydroxyl groups capable of reacting with the o-dianisidine. The exact mechanism whereby the surface inorganic reacts with the organic compound is not fully understood although the bond formed was found to be quite strong. For example, the bond could not be washed off with 0.5 M sodium chloride, boiling water, or urea.

For reasons of economy, convenience, and control of surface area, and, where desired, porosity, we prefer siliceous support materials, consisting mainly of silica. Silica per se, glass, and porous glass or fritted glass are all useful supports and can be readily surface activated and coated with o-dianisidine from either an aqueous or organic solvent.

After the inorganic support has been reacted with the o-dianisidine solution to form a surface coating of o-dianisidine residues, the coated support can be reacted directly with a protein solution or, where desired, indirectly with the solution after some further modification. For example, in some of the examples below, glutaraldehyde was found to be an excellent modifier between the o-dianisidine residue and the proteins of the protein solution, thus permitting a relatively mild protein bonding step. Where it is desirable to space the protein away from the support a "coupling arm" of o-dianisidine and modifiers can be extended by simply alternating the reaction of o-dianisidine and modifiers such as glutaraldehyde.

In general, the reactions using the o-dianisidine are relatively rapid, an obvious advantage. The o-dianisidine molecule, somewhat similar to the BMBD of U.S. Pat. No. 3,930,951, cited above, has the following structure:

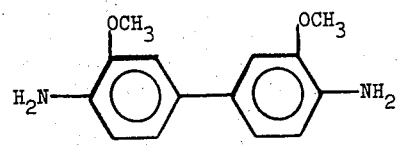

The compound can be applied in an aqueous solution or in such solvents as methanol. In either case, the concentration used can be fairly small, preferably about 1% by weight. The reaction can be completed in about 10 minutes and can be done at room temperature. Once an o-dianisidine residue has been formed on the inorganic surface, the treated support may be reacted directly with the aqueous protein solution in which case it is thought that the available amino group of the o-dianisidine residue reacts with available reactive groups (e.g. —COOH) on all proteins.

Alternatively, the o-dianisidine residue is modified with a modifier such as glutaradlehyde to tailor-make a surface for subsequent reaction with the protein. For example, in some cases, to protect an active site on an enzyme or complexing site on an antibody, it may be desirable to modify the available amino groups of the o-dianisidine to form a non-interfering group capable of bonding with the protein.

The proteins which can be usefully immobilized according to this disclosure include any polypeptides which, when immobilized according to the teachings herein, will retain a useful function (e.g. biological activity). In the case of antibodies, complexing ability or affinity for antigenic substances or haptens must be preserved. Examples of the wide variety of both enzymes and antibodies and proteinaceous antigenic substances which can be bonded according to this disclosure can be found in U.S. Pat. No. 3,519,538, (enzymes) and U.S. Pat. No. 3,652,761, (antibodies and antigenic substances).

In the examples below, we describe the bonding of a variety of enzymes and one antibody to a variety of inorganic carriers and then demonstrate retention of the respective biological activities. In some preliminary experiments, o-dianisidine was attached to the surfaces of porous silica, controlled pore porous glass (CPG) and fine fritted glass using a 1% o-dianisidine aqueous solution containing 0.7 ml HCl per 100 ml of solution.

In some cases, the surface modified siliceous materials were washed and then converted to materials having surface aldehyde groups by the addition of glutaraldehyde. The aldehyde derivative was then washed. To various samples of these derivatives enzymes such as papain, lactase and catalase were attached. The papain composite was then shown to have enzymatic activity with casein. Catalase activity was demonstrated with peroxide solution. Alkaline *Bacillus subtilis* protease was attached directly to the o-dianisidine derivative of the porous silica and then shown to have retained enzymatic activity by use of casein.

PREPARATION OF SURFACE DERIVATIVES

The inorganic surfaces can be readily derivatized via both aqueous and organic solvents.

METHOD 1

Aqueous Solution Preparation

For this method, the carrier material consisted of porous silica particles (45 to 80 mesh) having a surface area of 40 m$^2$/g and an average pore diameter of 425A. The minimum pore diameter was 270A and the maximum diameter was 475A. The o-dianisidine solution consisted of 5 grams of o-dianisidine plus 4 ml HCl diluted to 500 ml with water.

A 100 gram sample of the silica was transferred to a coarse, 350 ml fritted glass funnel. To this sample, 200 ml of the o-dianisidine solution was delivered at a rate of 1000 ml per hour. The o-dianisidine was trapped at the top surface of the silica and the solution came through clear. After delivery of the 200 ml was completed, the silica cake was drained. An additional 200 ml of the o-dianisidine was delivered to the silica. Again, after passage through the silica, the solution was colorless. After the second delivery, isopropanol was delivered to the derivative to wash away excess o-dianisidine. The first 100 ml of alcohol delivered was intensely colored brownish-red; however, after a second 100 ml volume of the alcohol was delivered, the wash solution began to lose color. The support was then washed with 300 ml of water followed by another 100 ml of isopropanol and, finally, washed with 100 ml of acetone and then air dried with aspiration for 1 hour. The carrier derivative was transferred to a glass bottle and used subsequently for preparing the immobilized proteins.

METHOD 2

Organic Solution Preparation

For this procedure, the inorganic support consisted of silica particles having a surface area of 370 m$^2$/g and an average particle size of about 4 microns (Syloid 72, Grace Div., Davidson Chem. Co.). The o-dianisidine solution consisted of one gram of o-dianisidine diluted to 100 ml with methanol. The carrier was prepared by mixing 20 grams of the silica with 100 ml of the o-dianisidine solution in a 150 ml beaker for 10 minutes at room temperature. The slurry was transferred to a fine frit 600 ml funnel and filtered with aspiration on a filter flask. The solution came through the funnel with about 50% of the color of the original solution. The silica was then washed on the funnel with aspiration with 100 ml of methanol. The filtrate was clear. The carrier derivative was then washed with 50 ml of acetone and air dried. Samples of this carrier were used for the immobilization of antibodies, described below.

Another sample of the same carrier was derivatized further for aldehyde function as follows: To 3.64 grams of the above-described treated carrier, 18.2 ml of a 2.5% aqueous glutaraldehyde solution was added in a 30 ml beaker and stirred for about 10 minutes. This derivative was then immediately filtered with aspiration on a Buchner funnel containing S and S576 filter paper. The derivative was then washed with 100 ml of distilled water and finally washed with 50 ml of acetone and air dried.

The immobilization of enzymes is described in Examples I–III below. Example IV illustrates the immobilization of an antibody.

EXAMPLE I

Immobilized Glucose Oxidase and Catalase

A 10 mm fritted glass disc was placed in a 5 ml beaker. One ml of the 1% o-dianisidine solution containing HCl (described above) was added to the beaker which was then placed on a hot plate for one minute. As the solution came to a boil, the disc was removed from the beaker and held under a distilled water faucet for one minute. The disc was then placed in a 5 ml beaker to which 3 ml of water and 0.1 ml of glutaraldehyde was added and allowed to react with hand shaking for 1 minute. The disc was then washed by holding it under a distilled water faucet for one minute. The disc was replaced in a beaker and 3 ml of a glucose oxidase-catalase solution (Miles, DeeO) was added and reacted for 1 minute with mixing. The disc was removed from the beaker and held under the distilled water for one minute. The total time used for this preparation was about 11 minutes with an actual operation time of 6 minutes and a bonding time of about 3 minutes. This represents a significant improvement over many past bonding methods requiring longer preparation times. The above preparation was assayed for catalase activity by merely observing bubbles of $O_2$ produced from a 1% $H_2O_2$ solution. The $O_2$ bubbles were generated from the pores in a fine stream. The preparation was visually observed with 4 different aliquots of $H_2O_2$ with no diminution in the evaluation of $O_2$. Further information describing the advantages of immobilizing both glucose oxidase and catalase on the same carrier can be found in U.S. Pat. No. 3,841,971 to Messing wherein it is pointed out how the two enzymes act synergistically.

EXAMPLE II

Immobilized Lactase

Lactase derived from Escherichia coli was immobilized on the derivatized carrier of Method 1 by placing about 1.0 g of the carrier in a column and circulating through the column at 400 ml/hr about 12.5 ml of an aqueous slurry of the enzyme containing about 417 lactase activity units. The reaction was carried out at 20°C. with circulation for about 22 hours. It was found that the amount of enzyme immobilized yielded between 92 and 98 lactase units per gram. It is significant to note that in this preparation no further functionalization of the surface o-dianisidine residue was required. In the past, this level of activity per gram commonly required added processing steps — e.g. silanization of an inorganic followed by further functionalization with glutaraldehyde. In a subsequent experiment where the same carrier of Method 1 was further functionalized with glutaraldehyde, an enzyme loading of 261 lactase units per gram was achieved. When the carrier of Method 1 having the o-dianisidine residue was further functionalized to form a reactive diazonium group, the lactase loadings were about 197 lactase activity units per gram.

EXAMPLE III

Immobilized Lactase From Aspergillis Niger (Column)

Two grams of o-dianisidine silica carrier described in Method 1 was transferred to a 9 × 150 mm water jacketed column. 30 ml of a 2.5% glutaraldehyde in water solution was circulated at 530 ml per hour in a downward flow through the column for 10 minutes. The flow was then reversed upward for an additional 10 minutes and reversed again downward for another 10 minutes. The glutaraldehyde was then removed from the column and 1 liter of water was pumped through the column at 530 ml per hour to wash the derivative. The derivative was then ready for coupling.

30 ml of a lactase solution (500ml lactase diluted to 30 ml with water and containing 5619 lactase units was circulated in a downward flow through the column at 530 ml per hour at room temperature. This circulation was continued for approximately 17 hours, after which the enzyme was removed from circulation and the column was washed with 100 ml of water at approximately 70 ml per hour flow rate. The enzyme was then washed on the column with 50 ml of 0.5 M sodium chloride followed by an additional 20 ml of water. The total volume of washes and enzyme solution was approximately 200 ml. This wash plus enzyme solution was assayed and found to contain 1570 units of lactase activity in a 200 ml sample.

The immobilized enzyme was evaluated in the same column without removal from the column as was used for preparing the enzyme. The substrate solution contained 200 gms of lactose plus 3800 ml of water plus 1.3 ml of 2 M HCl and the pH of this solution was 3.5. The column was maintained continually at 50°C. with a circulating water bath. The feed rate at which the substrate was supplied to the column was between 49 and 71 ml per hour. This column was fed continuously over a 56 day period. Approximately twice a week, the column and pump were washed with 100 ml of 0.17 M acetic acid to remove microbial growth within the pump and on the column. The results were as follows:

TABLE I

| DAYS | ACTIVITY (U/g) |
|---|---|
| 0 | 620 |
| 1 | 619 |
| 2 | 650 |
| 6 | 535 |
| 7 | 565 |
| 8 | 488 |
| 14 | 465 |
| 16 | 553 |
| 23 | 357 |
| 27 | 451 |
| 28 | 369 |

TABLE I-continued

| DAYS | ACTIVITY (U/g) |
|---|---|
| 29 | 484 |
| 34 | 421 |
| 35 | 413 |
| 36 | 428 |
| 41 | 347 |
| 42 | 383 |
| 51 | 316 |
| 55 | 285 |
| 56 | 273 |

It should be noted in the table above, that the low results achieved were on those days where the column had not been washed for considerable lengths of time and substantial growth was noted both in the column and in the substrate feed. On the days when the feed was clear within 4 days after washing the column, the activities were rather substantial. The results of the activities were plotted, and the half-life of this column was found to be 52 days with an LCL (95%) of 43 days and UCL (95%) of 65 days.

The activity recovery for the preparation of this enzyme is as follows: Enzyme recovery = [(2 × 620) + 1570] ÷ 5619 × 100 = 50%. The coupling efficiency for this preparation is as follows: Coupling efficiency = (620 × 2) ÷ (5619 − 1570) × 100 = 31%.

EXAMPLE IV

Immobilized Antibodies (anti-thyroxine)

A representative antibody (anti-thyroxine or anti-$T_4$) useful in the radioimmunoassay (RIA) of $T_4$ was immobilized and found to retain its immunochemical complexing properties.

Preparation of the Immobilized Antibody (IMA)

Silica particles were derivatized with o-dianisidine by Method No. 2. After drying, 1.0 gm of the carrier was diazotized with sodium nitrite. After diazotization the derivative was washed several times with borate (0.03M) buffered saline (0.15M) pH 8.0. The derivative was then reacted with 1.5 ml of $T_4$ antisera (titer 1:10000) at 4°C. with stirring. The pH was maintained between 8.0 – 8.5 with 0.1N NaOH. After 30 minutes the pH stabilized at 8.2 and the reaction was stirred slowly at 4°C. overnight. After this time the composite gave a negative β-napthol test indicating no more remaining functional diazo groups. The preparation was then washed (4X) with phosphate-buffer (0.03M) saline (0.15M) containing 0.1% bovine serum albumin (PBS-BSA).

Titering of the Immobilized Antibody

The derivative was diluted in PBS-BSA to contain 10 mgs. of IMA per ml. The IMA (0.1 ml) was serially diluted with PBS-BSA in 12 × 75 polystyrene tubes. Each tube then would contain 0.1 ml of PBS-BSA containing 100 ug of 8-anilino-1-napthalene sulfonic acid (ANS) and finally 0.1 ml of labeled $T_4$ (~25,000 c.p.m.). The tubes were vortexed and incubated at 37°C. for 2.0 hours. Appropriate controls were run to account for non-specific binding. At this time the tubes were centrifuged (15 minutes at 5000 r.p.m.) and the supernatant decanted into duplicated tubes and both tubes counted in the gamma spectrometer. The per cent of label bound was calculated. A typical titer curve was made where per cent bound was expressed as a function of final dilution. As a control 1.0 gm of silica was stirred at pH 8.0 overnight with antisera. Titering of this control preparation indicated little or no antibody attached to the particles.

Assay of $T_4$ Using the IMA

A dilution of IMA was chosen so that 0.1 ml bound between 50–60% of the labeled material added. This quantity was added to duplicate 12 × 75 tubes. To this was added 0.1 ml of $T_4$ free serum, 0.1 ml of $T_4$ standards (12.5–400 ng/ml), 0.6 ml of PBS-BSA containing 200 ng of ANS and finally 0.1 ml of labeled $T_4$. The tubes were vortexed and incubated at 37°C. for 12 hours. At this time, the tubes were centrifuged, decanted into duplicate tubes and counted for 1.0 minutes on the gamma spectrometer. A typical dose response curve was prepared.

Three commercially available analyzed control sera, (A), (B), and (C) were assayed and Table II shows the good correlation of results.

TABLE II

| Control | Calculated | Assayed (Found) |
|---------|------------|-----------------|
| (A)     | 121        | 126             |
| (B)     | 72         | 71              |
| (C)     | 80         | 92              |

Standard curves were prepared for measuring $T_4$ in a clinically significant concentration range and these curves were compared with standard curves obtained using immobilized anti-$T_4$ coupled via a silane coupling agent to glass particles. The curves were substantially the same within that concentration range.

From the above experiments, it is clear that biologically active proteins such as enzymes and antibodies can be successfully immobilized according to the novel method disclosed herein. Since the disclosed method is subject to modifications, it is intended that the scope of the disclosed invention should be limited only by the following claims.

We claim:

1. A method of bonding a biologically active protein to an inorganic support material to prepare an immobilized protein-support composite, the method comprising the steps of
    a. reacting a high surface area, water insoluble inorganic material having available surface oxide or hydroxyl groups with a solution of o-dianisidine to form residues of o-dianisidine on the surface; and
    b. reacting the reaction product of step (a) with an aqueous solution of the protein.
2. The method of claim 1 wherein the protein of step (b) is selected from enzymes and antibodies.
3. The method of claim 2 wherein the protein is an enzyme selected from lactase, *Bacillus subtilis* protease, and catalase.
4. The method of claim 2 wherein the protein is an antibody to thyroxine.
5. The method of claim 1 wherein the inorganic material is siliceous.
6. The method of claim 5 wherein the siliceous material is in particulate form having a surface area of at least about 0.2 m²/g and selected from silica, porous glass, and fritted glass.
7. The method of claim 1 wherein the o-dianisidine is in an aqueous solution.
8. The method of claim 1 wherein the o-dianisidine is in an organic solution.
9. The method of claim 1 wherein after the reaction of step (a) but prior to the reaction of step (b) the reaction product of step (a) is reacted with a glutaraldehyde solution.
10. The method of claim 1 wherein after the reaction of step (a) but prior to the reaction of step (b) the reaction product of step (a) is diazotized.
11. An immobilized protein composite comprising a biologically active protein bonded via an o-dianisidine residue to a high surface area, essentially water insoluble inorganic material in accordance with the method of claim 1.
12. The composite of claim 11 wherein the protein is selected from enzymes and antibodies.

* * * * *

UNITED STATES PATENT AND TRADEMARK OFFICE
CERTIFICATE OF CORRECTION

PATENT NO. : 3,983,000
DATED : September 28, 1976
INVENTOR(S) : Ralph A. Messing and Gerald Odstrchel It is certified that error appears in the above-identified patent and that said Letters Patent are hereby corrected as shown below:

Column 5, line 30, "(500 ml" should be -- (500 mg --.

Signed and Sealed this

First Day of March 1977

[SEAL]

Attest:

RUTH C. MASON
Attesting Officer

C. MARSHALL DANN
Commissioner of Patents and Trademarks